(12) United States Patent
Abbott

(10) Patent No.: US 10,258,276 B2
(45) Date of Patent: Apr. 16, 2019

(54) BREATHALYZER COACHING AND SETUP METHODOLOGY

(71) Applicant: Now Group UK Ltd, Maidenhead (GB)

(72) Inventor: Hunter David Abbott, Bray (GB)

(73) Assignee: Now Group UK Ltd, Maidenhead (GB)

( * ) Notice: Subject to any disclaimer, the term of this patent is extended or adjusted under 35 U.S.C. 154(b) by 147 days.

(21) Appl. No.: 15/296,446

(22) Filed: Oct. 18, 2016

(65) Prior Publication Data

US 2017/0105674 A1    Apr. 20, 2017

(30) Foreign Application Priority Data

Oct. 20, 2015    (GB) .................................... 1518600

(51) Int. Cl.
| | | |
|---|---|---|
| *A63F 9/24* | (2006.01) | |
| *A61B 5/00* | (2006.01) | |
| *A61B 5/08* | (2006.01) | |
| *A61B 5/087* | (2006.01) | |
| *A61B 5/091* | (2006.01) | |
| *G01N 33/497* | (2006.01) | |
| *A61B 10/00* | (2006.01) | |

(52) U.S. Cl.
CPC ............ *A61B 5/486* (2013.01); *A61B 5/0022* (2013.01); *A61B 5/082* (2013.01); *A61B 5/087* (2013.01); *A61B 5/091* (2013.01); *A61B 5/4845* (2013.01); *A61B 5/6898* (2013.01); *A61B 5/7221* (2013.01); *A61B 5/742* (2013.01); *G01N 33/4972* (2013.01); *A61B 2010/0009* (2013.01); *A61B 2010/0087* (2013.01)

(58) Field of Classification Search
CPC .... A61B 5/0022; A61B 5/0486; A61B 5/4875
See application file for complete search history.

(56) References Cited

U.S. PATENT DOCUMENTS

2003/0176803 A1* 9/2003 Gollar .................... A61B 5/097
                                                              600/532
2005/0009195 A1* 1/2005 Wang ................. G01N 33/4972
                                                              436/132

(Continued)

FOREIGN PATENT DOCUMENTS

| FR | 2577677 | 8/1986 |
|---|---|---|
| WO | 02/12883 | 2/2002 |
| WO | 2014/146714 | 9/2014 |

OTHER PUBLICATIONS

FindLaw.com, "Comparing State DUI Laws", pp. 1-4, Oct. 11, 2014, at https://web.archive.org/web/20141011033213/http://dui.findlaw.com:80/dui-laws-resources/comparing-state-dui-laws.html (last accessed Jul. 30, 2018).*

(Continued)

*Primary Examiner* — Steve Rowland
(74) *Attorney, Agent, or Firm* — Stoel Rives LLP; Zhi-Xiang Oh

(57) ABSTRACT

Methods of coaching a user of a breathalyzer to make use of correct blowing technique when blowing into the breathalyzer are provided. Methods of setting up a breathalyzer such that it adjusts a breathalyzer's parameters to account for jurisdictional variations in blood and/or breath alcohol limits and other standards are also provided.

6 Claims, 3 Drawing Sheets

(56) References Cited

U.S. PATENT DOCUMENTS

| | | | | |
|---|---|---|---|---|
| 2005/0241871 A1* | 11/2005 | Stewart | ............... | B60K 28/063 |
| | | | | 180/272 |
| 2007/0144812 A1* | 6/2007 | Stewart | ............... | B60K 28/063 |
| | | | | 180/272 |
| 2011/0084820 A1* | 4/2011 | Walter | ............... | B60K 28/063 |
| | | | | 340/426.24 |
| 2011/0309932 A1* | 12/2011 | Arringdale | ........... | B60K 28/063 |
| | | | | 340/539.14 |
| 2016/0363582 A1* | 12/2016 | Blackley | ............. | G01N 33/497 |
| 2017/0023453 A1* | 1/2017 | Hill, Jr. | ................ | G01N 1/4022 |

OTHER PUBLICATIONS

European Search Report Completed Sep. 1, 2017 Received in European Application 16193008.

Novak, Tristan et al., "Design and characterization of breath analysis system for BAC prediction" 2015 IEEE Virtual Conference on Applications of Commercial Sensors (VCACS), IEEE, (Mar. 15, 2015), pp. 1-5.

Partial European Search Report Completed Mar. 16, 2017 Received in European Application 16193008.

* cited by examiner

BREATHALYZER COACHING AND SETUP METHODOLOGY

RELATED APPLICATIONS

This application claims the benefit of United Kingdom Patent Application No. GB1518600.0, filed Oct. 20, 2015, which is hereby incorporated by reference in its entirety.

SUMMARY

The present disclosure relates to methods of coaching a user of a breathalyzer to make use of correct blowing technique when blowing into the breathalyzer. Methods of setting up a breathalyzer such that it adjusts a breathalyzer's parameters to account for jurisdictional variations in blood and/or breath alcohol limits and/or other standards are also described.

Although the present disclosure is described primarily with reference to a breathalyzer used by drivers of vehicles, it equally applies to breathalyzers used for other purposes such as, e.g., workforce or offender monitoring, etc.

In order to quickly determine whether a person has no, or sufficiently low, levels of alcohol in their bloodstream to safely operate said vehicle most jurisdictions/organizations have adopted certain Blood Alcohol Content (BAC) or Breath Alcohol Content (BrAC) upper thresholds.

Several different types of breathalyzer's exist to detect a person's BAC/BrAC; however, many of these suffer from inaccuracies that make them unreliable and sometimes difficult to use. For instance, some known breathalyzers do not monitor the pressure/volume/flowrate of the user's breath sample and do not therefore display any error message when used incorrectly. This can lead to erroneous results and consequent possible adverse repercussions unbeknown to the user. Some known breathalyzers do monitor the pressure/volume/flowrate of the sample provided by the user and provide a generic error message if these values are causing any errors in the reading obtained; this means that these devices can be difficult and frustrating to use since an untrained or inexperienced user does not know which aspect of the breath sample is causing a problem with the reading, or what is required to correct it.

According to a first aspect of the present disclosure there is provided a breathalyzer coaching methodology for coaching a user of a breathalyzer to make use of correct blowing technique, the method comprising:

gathering a sample breath provided by a user;

determining the instantaneous volume V, flowrate F and pressure P of the sample breath as it is being provided by the user;

determining whether the determined sample breath instantaneous volume V is less than a minimum threshold breath sample volume V1;

determining whether the determined sample breath instantaneous flowrate F is greater than a maximum threshold breath sample flowrate FMAX, between a maximum threshold breath sample flowrate and a minimum threshold breath sample flowrate FMIN, or less than the minimum sample breath flowrate FMIN;

determining whether the determined sample breath instantaneous pressure P is greater than a maximum threshold breath sample pressure PMAX, between a maximum threshold breath sample pressure and a minimum threshold breath sample pressure PMIN, or less than the minimum sample breath pressure PMIN; and forming a diagnosis of any problems with the user's blowing technique based on said detected instantaneous volume V, flowrate F or pressure P values and providing at least a corrective coaching message to the user depending upon said diagnosis.

Another problem with existing breathalyzers is that a breathalyzer designed to be used in one jurisdiction (country/region) may give misleading results if used in other jurisdictions due to differing BAC/BrAC Ratios (BER) and other differences in parameters stipulated by differing jurisdictions. Furthermore, one breathalyzer cannot currently comply with multiple national or international standards since adjusting many of the required parameters requires specialist knowledge or for the breathalyzer to be returned to the manufacturer for adjustment and re-certification. This causes issues for users who may wish to use their breathalyzer in several countries and presents stocking and manufacturing complications for the breathalyzer manufacturers and their supply chain.

According to a second aspect of the present disclosure there is provided a method of adjusting a breathalyzer unit's parameters to account for variations in jurisdictional legal requirements and any prevailing breathalyzer standard in place in the jurisdiction, the method comprising: displaying to a user a list of individual entries for a plurality of jurisdictions and associated legal requirements and any prevailing breathalyzer standard in place in the jurisdiction, said individual entries having preloaded data relating to first and second tier jurisdictional legal requirements and any prevailing breathalyzer standard in place in the jurisdiction, and an identifier title referring to said first and second tier jurisdictional legal requirements and any prevailing breathalyzer standard in place in the jurisdiction such that a user may select the appropriate jurisdiction and associated first and second tier jurisdictional legal requirements and any prevailing breathalyzer standard in place in the jurisdiction by selecting an individual entry from said list by way of the identifier title.

Further features and advantages of the first and second aspects of the present disclosure will become apparent from the claims and the following description.

BRIEF DESCRIPTION OF THE DRAWINGS

Embodiments of the present disclosure will now be described by way of example only, with reference to the following diagrams, in which.

DETAILED DESCRIPTION

Figure 3:
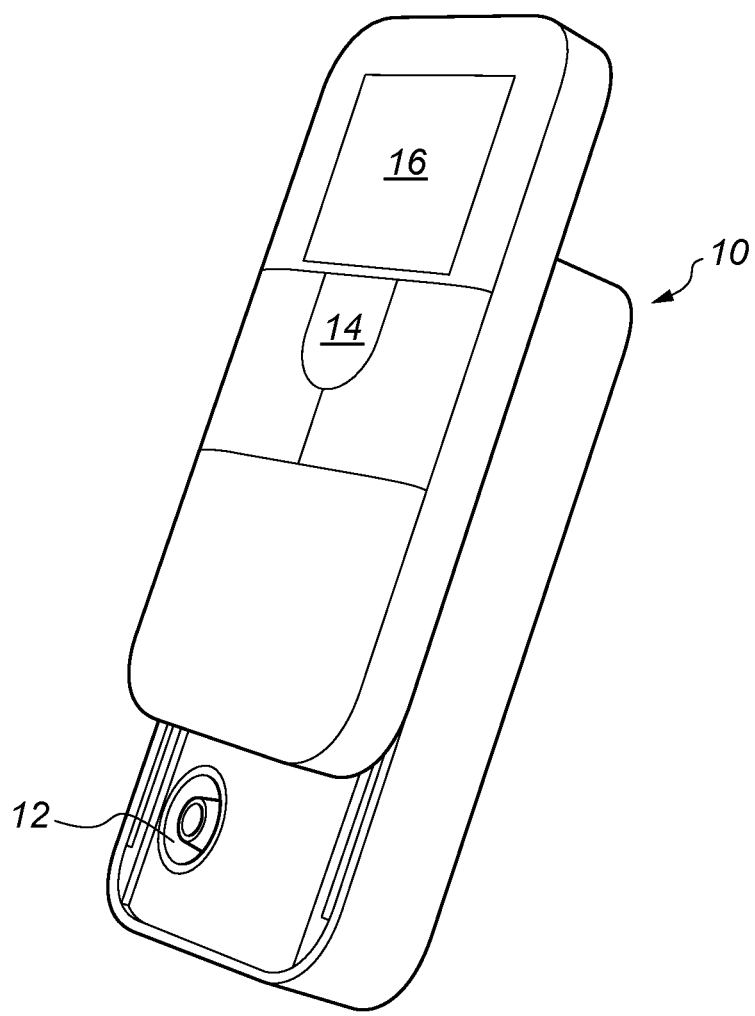
FIG. 3 is a schematic illustration of a breathalyzer which is provided with the systems of the present disclosure.

As illustrated in FIG. 3, the methods subsequently described may be provided by a battery powered hand-held breathalyzer unit 10 having a breath sampling inlet 12, a power button 14 and a message display screen 16. The breathalyzer unit 10 is fitted with one or more sensors that are capable of determining the volume, instantaneous flow rate and pressure of air blown into the inlet 12 at any instant by the user during the sampling event.

Figure 1:
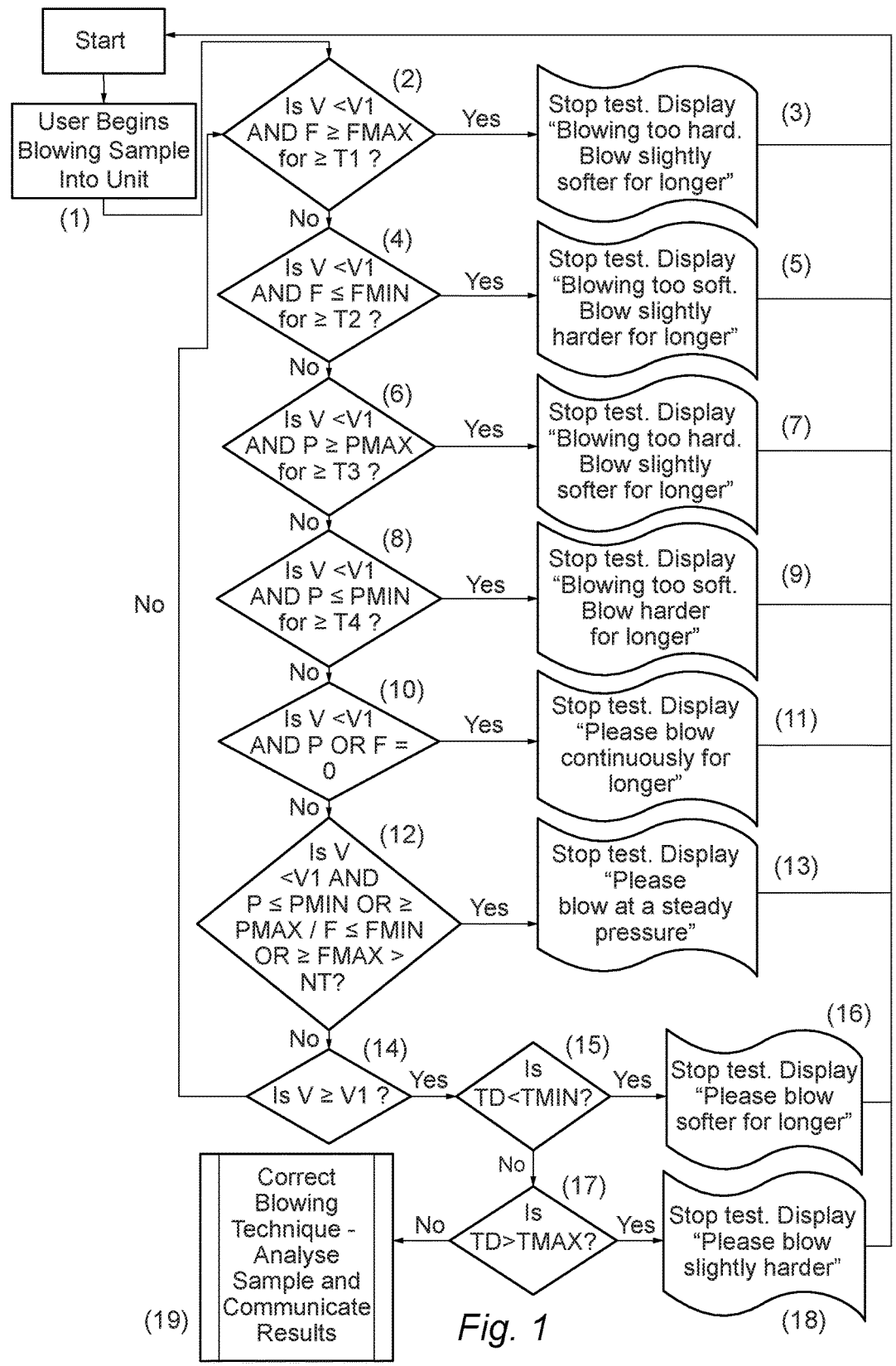
FIG. 1 is a flow diagram illustrating a breathalyzer coaching methodology of the first aspect of the present disclosure.

With reference to step 1 of FIG. 1, a user first blows into the breathalyzer unit. Whilst blowing into the unit, the logic steps 2, 4, 6, 8, 10, 12, 14 (discussed subsequently) are cycled through repeatedly in order to monitor the blowing parameters of the sample whilst it is being gathered. If any incorrect blowing technique is being applied the test is stopped as soon as that is detected and the user is notified accordingly.

At each of steps 2, 4, 6, 8, 10, 12, 14 the sensors of the unit determine the instantaneous volume V obtained at that point in the sampling event and determine whether this is less than a minimum required threshold breath sample volume V1. Lf V is less than V1 (i.e. an insufficient total volume of air has been provided by the user at that stage of the sampling event and the sampling event is therefore still ongoing) then a series of AND logic steps are performed in steps 2, 4, 6, 8, 10, 12 in order to continually monitor whether the pressure and flowrate of the sample are within pressure and flowrate parameters. In this way, step 14 (where V is greater than or equal to V1) can only be reached if the other checks of steps 2, 4, 6, 8, 10, 12 have been successfully passed.

At step 2 of FIG. 1, an assessment is made of whether V is less than V1 AND the sampled flowrate F is greater than or equal to FMAX for greater than or equal to a length of time T1 (such as e.g. 0.5 seconds). If this is the case then the test is immediately stopped and a correcting coaching message communicating this fact to the user is displayed at step 3. For example the message may declare "Blowing too hard. Blow slightly softer for longer". The "slightly softer" terminology referring to FMAX having been exceeded for greater than T1. If the flow rate F is not greater than FMAX for greater than T1 then step 4 is carried out next as described below.

At step 4 of FIG. 1, an assessment is made of whether V continues to be less than V1 AND the sampled flowrate F is less than or equal to a minimum permissible flowrate value FMIN for greater than or equal to a length of time T2 (such as e.g. 0.5 seconds). If this is the case then the test is immediately stopped and a correcting coaching message communicating this fact to the user is displayed at step 5. For example the message may declare "Blowing too soft. Blow slightly harder for longer". The "slightly harder" terminology referring to FMIN having been exceeded for greater than T2. If the flow rate F is not less than or equal to FMIN for greater than T2 then step 6 is carried out next as described below.

At step 6 of FIG. 1, an assessment is made of whether V continues to be less than V1 AND the sampled pressure P is greater than or equal to a maximum permissible pressure value PMAX for greater than or equal to a length of time T3 (such as e.g. 0.5 seconds). If this is the case then the test is immediately stopped and a correcting coaching message communicating this fact to the user is displayed at step 7. For example the message may declare "Blowing too hard. Blow slightly softer for longer". The "slightly softer" terminology referring to PMAX having been exceeded for greater than T3. If the pressure P is not greater than or equal to PMAX for greater than T3 then step 8 is carried out next as described below.

At step 8 of FIG. 1, an assessment is made of whether V continues to be less than V1 AND the sampled pressure P is less than or equal to a minimum permissible pressure value PMIN for greater than or equal to a length of time T4 [such as e.g. 0.5 seconds). If this is the case then the test is immediately stopped and a correcting coaching message communicating this fact to the user is displayed at step 9. For example the message may declare "Blowing too soft. Blow slightly harder for longer. The slightly harder" terminology referring to PMIN having been exceeded for greater than T4. If the pressure P is not less than or equal to PMIN for greater than T4 then step 10 is carried out next as described below.

At step 10 of FIG. 1, an assessment is made of whether V continues to be less than V1 AND whether either the sampled pressure P or the sampled flowrate F is equal to or near zero (Le. where the user has stopped blowing). If this is the case then the test is immediately stopped and a correcting coaching message communicating this fact to the user is displayed at step 11. For example the message may declare "Please blow continuously for longer". If the pressure P and flowrate F do not equal zero then step 12 is carried out next as described below.

At step 12 an assessment is made of whether V continues to be less than V1 AND of the number N of times in total during the sampling event the pressure P or flowrate F have been determined to breach the respective PMAX, PMIN, FMAX, FMIN threshold parameters) regardless of whether or not this has occurred over a shorter duration than times T1, T2, T3, T4. This is then compared to a pre-set maximum threshold number of breaches NT. If N is greater than NT (where for example the user has blown relatively steadily but has in fact breached the parameters for very short periods of time) the test is immediately stopped and a correcting coaching message communicating this fact to the user is displayed at step 13. For example the message may declare "Please blow at a steady pressure".

This acts as an additional check which catches any anomalies in the sample that could otherwise create a "pass" result for each of the other steps described above. If N is less than NT [e.g. where there is no unsteadiness in the breath flowrate/pressure or where there have only been a small number of short parameter breaches) then step 14 is carried out next as described below.

At step 14, the sample has passed each of the assessments in steps 2, 4, 6, 8, 10 and 12 and a check is then made to determine if the volume V obtained at that instant is greater than or equal to V1. If it is not then the logic recycles to step 2 for continued cycled monitoring by repeating steps 2, 4, 6, 8, 10 and 12. This cycle is rapidly repeated until such time as V is greater than or equal to V1 at which point step 15 is then carried out next.

Since some jurisdictions stipulate that breathalyzer sampling must occur over a certain minimum (TMIN) or maximum (TMAX) sampling duration, at step 15 an assessment is made on whether the Total Duration (TD) of the sampling event [e.g. the amount of time the user has been blowing into the unit) is less than TMIN. If this is the case then a correcting coaching message communicating this fact to the user is displayed at step 16. For example the message may declare "Please blow softer for longer". If TD is not less than TMIN then step 17 is carried out next as described below.

At step 17, an assessment is made on whether the Total Duration (TD) of the sampling event is greater than TMAX. If this is the case then a correcting coaching message communicating this fact to the user is displayed at step 18. For example the message may declare "Please blow slightly harder." If TD is not greater than TMAX then all of the validations at logic steps 2, 4, 6, 8, 10, 12, 14, 15 and 17 have been passed and the unit determines that the correct blowing technique must therefore have been applied throughout the sampling event. The obtained breath sample is therefore then measured and the results communicated to the user at step 19.

The above blow coaching methodology provides a greatly enhanced user experience and more accurate and reliable testing results for any given sample obtained since it provides instantaneous monitoring and feedback to the user during the sampling event. Furthermore, the resulting device is user friendly and quicker to use than known products since fewer failed attempts occur. In addition, successfully collecting a breath sample without several failed attempts increases the accuracy of the reading obtained as several failed attempts will result in a temporary false lowering of the lung alcohol content of the user due to several deep lung exhalations and breaths.

Figure 2:
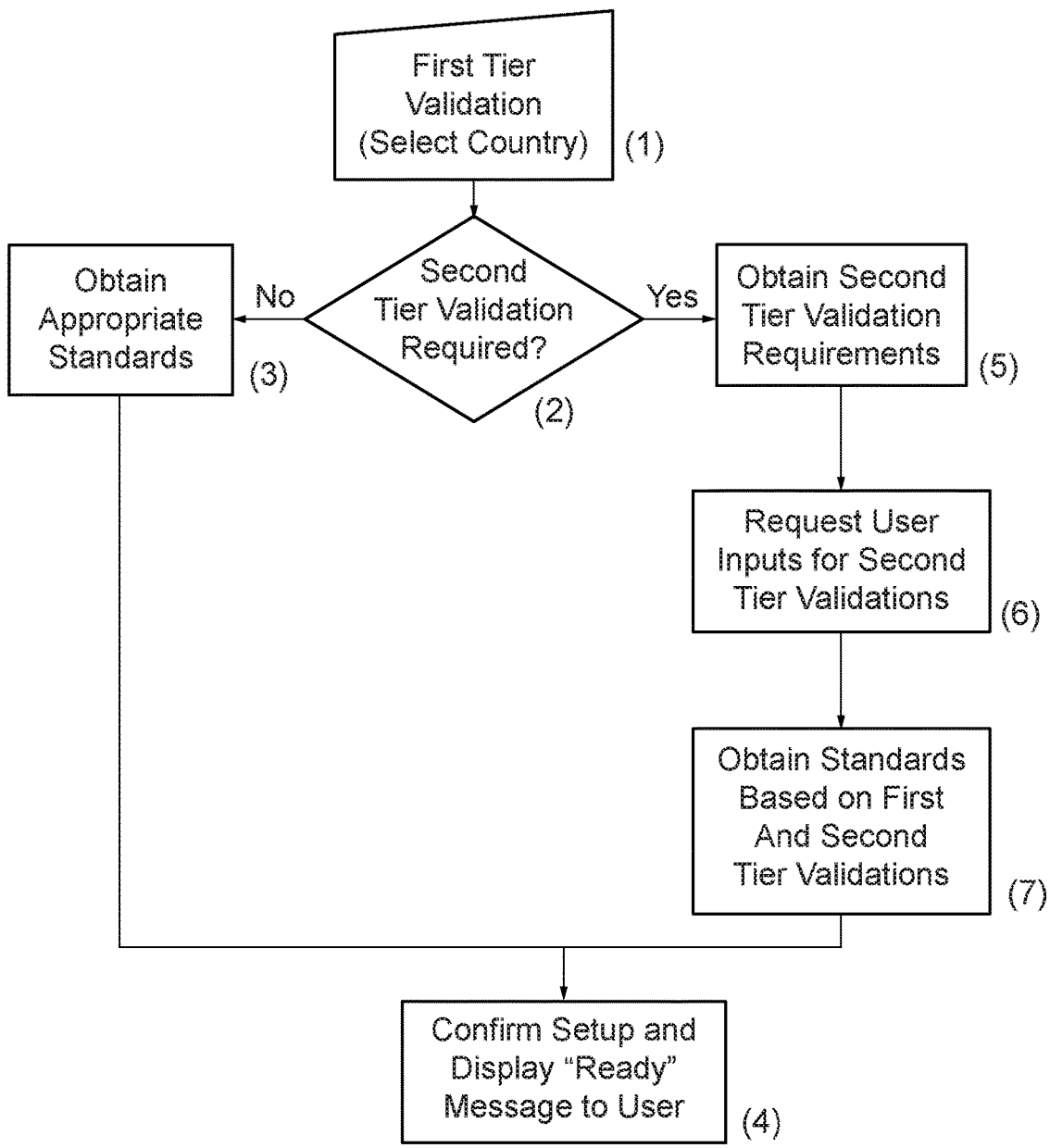
FIG. 2 is a flow diagram illustrating a method of adjusting a breathalyzer's parameters to account for variations in jurisdictional standards in accordance with the second aspect of the present disclosure.

With reference to FIG. 2 a method of adjusting a breathalyzer's parameters to automatically account for variations in jurisdictional BBR, BAC BrAC thresholds and other standards will now be described.

In accordance with this methodology, prior to the user blowing into the breathalyzer unit, they must first set up the unit depending upon their jurisdictional/geographical location e.g. whether they are driving in one country/region or another. In order to set up the unit the user is first asked which country or region they are driving in (or intend to drive in). This is input at step 1 as a first tier validation input. An example first tier validation input might be to select the country (e.g., the United Kingdom) from a list of preloaded countries.

After selecting the country at step 2, a cross-check is made as to whether that country has any second tier validation requirements which require user input. For instance these might include regional variations in BAC/BrAC thresholds or (where the selected region or country has more than one BAC/BrAC threshold) a selection of the BAC/BrAC threshold to be applied.

If the selected country has standards which do not require second tier validation from the user then the appropriate standards for that region are gathered from a database and applied to the breathalyzer at step 3.

Said database of standards to be applied may be remote from the breathalyzer (and hence accessed by wireless or wired means) or installed locally in the memory of the breathalyzer. The standards obtained may include e.g. the following:

The approved BBR to be applied in that jurisdiction in order to convert a Breath Alcohol Content (BrAC) reading to a Blood Alcohol Content (BAC) reading. This is necessary because some jurisdictions require the breath alcohol content result to be converted to an estimated blood alcohol content using an approved BBR. Different jurisdictions have adopted their own assumed/approved BBR when preparing their legislation—for instance [at the time of writing] this ratio is 2000:1 in France and Scandinavia; 2100:1 in the USA, Australia and Korea; and 2300:1 in the United Kingdom, Malaysia and Republic of Ireland. If the incorrect BBR is relied on in the wrong jurisdiction then the breathalyzer will display incorrect BAC results.

The unit of measure to be applied in that jurisdiction. This is necessary because different jurisdictions use different units of measure to display the test result. Some jurisdictions require the result to be displayed as a BAC reading (which requires conversion from a BrAC reading), whereas others require or accept the result to be displayed as a raw BrAC reading. Furthermore BrAC and BAC readings have several different units of measure and certain jurisdictions will require readings to be displayed in one unit of measure whereas others will require readings to be displayed in a different unit of measure.

The BrAC/BAC thresholds which apply to that jurisdiction. This is necessary because such thresholds vary from jurisdiction to jurisdiction due to corresponding variations in legislation. Indeed, in certain territories several different limits exist in even a single region for drivers of different types of vehicles, ages or levels of driving experience etc.

The volume of breath sample required. This is necessary because legislation in different jurisdictions require different minimum, maximum or specific volumes of breath to be exhaled through the breathalyzer by the user before a sample's alcohol concentration is analyzed. For example, the European EN 16280:2012 standard mandates that at least 1.2 liters of breath must be exhaled through the breathalyzer in any sampling event, whereas the Australian 3547-1997 standard mandates 1 liter.

The minimum and or maximum flow rate of the breath exhaled through the breathalyzer by the user to perform a successful test. This is necessary because different jurisdictions may require different minimum and maximum breath flow rates to comply with their national standards.

The minimum and or maximum duration that the user must blow the required sample volume through the breathalyzer in to perform a successful test. This is necessary because different jurisdictions may require different minimum and maximum values to comply with their national standards.

The prevailing national standard which may include information on a number of other parameters to be complied with which are specific to that jurisdiction and or national standard. For example, the European and Australian standards require a different method of displaying any results of a breathalyzer test, the method of rounding results and communicating those results.

At step 4, the user is then informed that the unit has been set up for the selected jurisdiction and is therefore ready to use in that jurisdiction.

In the event that the cross check at step 2 of FIG. 2 determines that second tier validation is required for the selected jurisdiction these are obtained at steps 5 and 6 prior to confirming the new settings. Examples of second tier validation inputs which might be obtained from the user at step 6 include e.g. a selection of the BrAC/BAC upper thresholds to be applied where the jurisdiction has more than one (e.g. the user may be asked to input their age, years of driving experience, type of vehicle etc. or select the option most appropriate to them from a list) or the specific region within the country they have selected (e.g. a user having selected the United Kingdom at step 1 may be asked to select from Scotland or England and Wales at step 6).

Based on the inputs provided by the user at steps 1 and 6, the appropriate standards are then gathered from a database and applied to the breathalyzer at step 4. Again, said database may be remote from the breathalyzer (and hence accessed by wireless or wired means) or installed locally in the memory of the breathalyzer. The standards obtained may include similar variables as outlined above in respect of the first tier validations; however, the values of these will have been selected depending upon the second tier validation inputs from the user at step 6.

The above described methodology allows a single breathalyzer to comply with several international standards and legislations so it can be used internationally with minimal effort and without the need for the user to have specialist knowledge, training or to return the item to the manufacturer's service center for adjustments. It ensures accurate readings in all jurisdictions regardless of differing BBRs and greatly reduces the risk of user confusion and applying incorrect settings which could lead to the breathalyzer giving inaccurate readings.

Although particular embodiments of the disclosure have been disclosed herein in detail, this has been done by way of example and for the purposes of illustration only. The aforementioned embodiments are not intended to be limiting with respect to the scope of the appended claims.

It is contemplated by the inventors that various substitutions, alterations, and modifications may be made to the disclosure without departing from the spirit and scope of the disclosure as defined by the claims.

Examples of these include the following:

Although in the embodiments described, the messages of the blow coaching methodology are described as being long-form text based messages displayed to a user, this information could be displayed in alternative formats. For example, the messages may be provided in an audible voice or sound message. Alternatively, the Visual display messages may be a table or icon based message system which provides "tick boxes" or other symbols to indicate which elements of the test have been passed in any sampling event, which elements have been failed in any sampling event and provides suggestions on how best the user can remedy any fails.

Rather than require the user to manually input the location of the driver/breathalyzer unit, the breathalyzer unit may be provided with locating means (such as on or off-board location sensors/GPS/smartphone interface etc.) which allows automatic determination of the unit location at any given time. Indeed, this may be a real-time or near real-time process which constantly assesses and applies the correct BrAC/BAG thresholds and other parameters for any given jurisdiction.

In the described embodiment of the method for adjusting a breathalyzer's parameters to automatically account for variations in jurisdictional BBR, BAC/BrAC thresholds, first and second tier validations are utilized; however, this could alternatively be achieved by combining the required variables into a single validation step by displaying several options for regions with second tier validation requirements at the first tier validation point. For example, the country list for the Netherlands could include two separate country listings from which the user can select—one for "Netherlands—Driver with Less Than 5 Years' Experience" and another for "Netherlands—Driver with More Than 5 Years' Experience".

Rather than steps 15 and 17, an alternative method of determining whether the user is blowing too hard or too softly is to calculate how long it is likely to take to obtain the required volume of breath sample based on the detected instantaneous flow rate values and the required volume of breath sample using the equation Time=Volume/Flowrate. Once the time has been calculated this can then be compared to the TMIN and TMAX values of the appropriate standard in order to immediately determine whether the user is likely to exceed these parameters and hence whether the user is blowing too hard or too softly.

The invention claimed is:

1. A method of adjusting a breathalyzer unit's parameters to account for variations in jurisdictional legal requirements and any prevailing breathalyzer standard in place in the jurisdiction, the method comprising:
displaying to a user a list of individual entries for a plurality of jurisdictions and associated legal requirements and any prevailing breathalyzer standard in place in the jurisdiction, said individual entries having preloaded data relating to first and second tier jurisdictional legal requirements and any prevailing breathalyzer standard in place in the jurisdiction, and an identifier title referring to said first and second tier jurisdictional legal requirements and any prevailing breathalyzer standard in place in the jurisdiction such that a user may select the appropriate jurisdiction and associated first and second tier jurisdictional legal requirements and any prevailing breathalyzer standard in place in the jurisdiction by selecting an individual entry from said list by way of the identifier title,
conducting a first tier validation process in order to gather details on the jurisdiction in which the breathalyzer is to be used; and dependent on the jurisdiction selected in the first tier validation process, determining whether said jurisdiction and or prevailing breathalyzer standard in place for the jurisdiction requires a second tier validation process to be performed; and
where it is determined that a second tier validation process is required, requesting second tier validation inputs from the user and then obtaining and applying jurisdictional legal requirements and any prevailing breathalyzer standard in place in the jurisdiction in accordance with said first and second tier validation inputs.

2. The method according to claim 1, wherein the step of conducting the first tier validation process comprises requesting at least a first tier validation input from the user, the first tier validation input comprising a request for the user to select a jurisdiction from an existing database of countries or regions and once selected, applying the appropriate standards and parameters to the breathalyzer including but not limited to Blood Breath Ratio (BBR), sampling criteria and other parameters required by the prevailing breathalyzer standard in the jurisdiction or by legal requirements.

3. The method according to claim 1, wherein the step of conducting the second tier validation process comprises requesting at least a second tier validation input from the user, the second tier validation input comprising at least one of alcohol BAC/BrAC thresholds, user age, experience or vehicle type.

4. The method according to claim 1, wherein the process of selecting the jurisdiction in the first tier validation process comprises automatically determining the location of the breathalyzer unit by way of locating means which instantaneously and/or continuously determine said location.

5. The method according to claim 4, wherein the step of using the locating means comprises using GPS signals, Wi-Fi location, Bluetooth location or other method of determining location.

6. A breathalyzer adapted to perform a method for adjusting the breathalyzer's parameters, the method comprising:
displaying to a user a list of individual entries for a plurality of jurisdictions and associated legal requirements and any prevailing breathalyzer standard in place in the jurisdiction, said individual entries having preloaded data relating to first and second tier jurisdictional legal requirements and any prevailing breathalyzer standard in place in the jurisdiction, and an identifier title referring to said first and second tier jurisdictional legal requirements and any prevailing breathalyzer standard in place in the jurisdiction such that a user may select the appropriate jurisdiction and associated first and second tier jurisdictional legal requirements and any prevailing breathalyzer standard in place in the jurisdiction by selecting an individual entry from said list by way of the identifier title, conducting a first tier validation process in order to gather details on the jurisdiction in which the breathalyzer is to be used; and dependent on the jurisdiction selected in the first tier validation process, determining whether said jurisdiction and or prevailing breathalyzer standard in place for the jurisdiction requires a second tier validation process to be performed; and where it is determined that a second tier validation process is required, requesting second tier validation inputs from the user and then obtaining and applying jurisdictional legal requirements and any prevailing breathalyzer standard in place in the jurisdiction in accordance with said first and second tier validation inputs.

\* \* \* \* \*